US011891627B2

(12) United States Patent
Shani et al.

(10) Patent No.: US 11,891,627 B2
(45) Date of Patent: Feb. 6, 2024

(54) MECHANICAL APPARATUS AND METHOD FOR ISOLATING STROMAL VASCULAR FRACTION

(71) Applicant: The Medical Research, Infrastructure, and Health Services Fund of the Tel Aviv Medical Center, Tel Aviv (IL)

(72) Inventors: Nir Shani, Ramat Hasharon (IL); Eyal Gur, Tel-Aviv (IL); Inna Solodeev, Ramat Gan (IL); Anna Aronovich, Tel Aviv (IL)

(73) Assignee: THE MEDICAL RESEARCH, INFRASTRUCTURE, AND HEALTH SERVICES FUND OF THE TEL AVIV MEDICAL CENTER, Tel Aviv (IL)

( * ) Notice: Subject to any disclaimer, the term of this patent is extended or adjusted under 35 U.S.C. 154(b) by 284 days.

(21) Appl. No.: 15/579,802

(22) PCT Filed: Jun. 9, 2016

(86) PCT No.: PCT/IL2016/050609
§ 371 (c)(1),
(2) Date: Dec. 5, 2017

(87) PCT Pub. No.: WO2016/199149
PCT Pub. Date: Dec. 15, 2016

(65) Prior Publication Data
US 2018/0155691 A1    Jun. 7, 2018

Related U.S. Application Data
(60) Provisional application No. 62/173,542, filed on Jun. 10, 2015.

(51) Int. Cl.
| | | |
|---|---|---|
| *C12N 5/0775* | (2010.01) | |
| *C12M 1/33* | (2006.01) | |
| *C12N 5/077* | (2010.01) | |
| *C12M 1/00* | (2006.01) | |
| *B01L 3/00* | (2006.01) | |
| *A61M 1/00* | (2006.01) | |

(52) U.S. Cl.
CPC ............ *C12N 5/0667* (2013.01); *A61M 1/80* (2021.05); *A61M 1/893* (2021.05); *B01L 3/502* (2013.01); *C12M 45/02* (2013.01); *C12M 47/04* (2013.01); *C12N 5/0653* (2013.01); *A61M 2202/08* (2013.01); *B01L 2300/0681* (2013.01); *B01L 2400/049* (2013.01); *B01L 2400/0478* (2013.01); *C12N 2527/00* (2013.01)

(58) Field of Classification Search
None
See application file for complete search history.

(56) References Cited

U.S. PATENT DOCUMENTS

| | | | |
|---|---|---|---|
| 2012/0264213 A1 | 10/2012 | Sand et al. | |
| 2013/0034524 A1* | 2/2013 | Agha-Mohammadi | ............ C12N 5/0667 424/93.7 |
| 2014/0017783 A1* | 1/2014 | Gimble | ........... C12N 5/0667 435/366 |
| 2015/0218521 A1* | 8/2015 | Soldati | ........... C12N 5/0667 435/377 |
| 2015/0231244 A1* | 8/2015 | Chi | ................ C12M 45/02 604/27 |

FOREIGN PATENT DOCUMENTS

| | | |
|---|---|---|
| WO | 2010/045389 A1 | 4/2010 |
| WO | 2011/117821 A1 | 9/2011 |
| WO | 2012/047286 A1 | 4/2012 |
| WO | 2013/144883 A2 | 10/2013 |
| WO | 2013/180952 A1 | 12/2013 |
| WO | 2014/016750 A1 | 1/2014 |
| WO | 2014/036094 A1 | 3/2014 |
| WO | 2014/138383 A1 | 9/2014 |
| WO | 2015/005871 A1 | 1/2015 |
| WO | 2018/044780 A1 | 3/2018 |

OTHER PUBLICATIONS

Aronowitz et al. Plast. Reconstr. Surg. 2013, 132:932e (Year: 2013).*
Smith et al., Bioanalysis 2012, 4(6), 741-749 (Year: 2012).*
Raposio et al.; Plast. Reconstr. Surg. 133: 1406, 2014 (Year: 2014).*
Alexander, "Understanding Mechanical Emulsification (Nanofat) Versus Enzymatic Isolation of Tissue Stromal Vascular Fraction (tSVF) Cells from Adipose Tissue: Potential Uses in Biocellular Regenerative Medicine", Journal of Prolotherapy, 2016, 8: e947-e960.
Aronowitz et al., "Mechanical versus enzymatic isolation of stromal vascular fraction cells from adipose tissue", SpringerPlus, (2015), 4:713, 9 pages.
Baptista et al., "An alternative method for isolation of mesenchymal stromal cells derived from lipoaspirate samples", Cytotherapy, (2009), vol. 11, No. 6, 706-715.
Doi et al., "Enrichment isolation of adipose-derived stem/stromal cells from the liquid portion of liposuction aspirates with the use of an adherent column", Cytotherapy, 2014; 16: 381-391.
Dubois et al., "Chapter 5: Isolation of Human Adipose-derived Stem Cells from Biopsies and Liposuction Specimens", Methods in Molecular Biology, vol. 449, Mesenchymal Stem Cells: Methods and Protocols, pp. 69-79.
Gimble et al., "Adipose-Derived Stem Cells for Regenerative Medicine", Circ Res. 2007; 100: 1249-1260.
(Continued)

*Primary Examiner* — Christopher M Babic
*Assistant Examiner* — Alyssa G Weston
(74) *Attorney, Agent, or Firm* — Vorys, Sater, Seymour and Pease LLP; Anthony P. Venturino (57) ABSTRACT

Provided is an apparatus and process for isolation of stromal vascular fraction (SVF) following lipoaspiration.

23 Claims, 7 Drawing Sheets

(56) References Cited

OTHER PUBLICATIONS

Granthos et al., "Chapter 3: A Method to Isolate and Purify Human Bone Marrow Stromal Stem Cells", Methods in Molecular Biology, vol. 449, Mesenchymal Stem Cells: Methods and Protocols, pp. 45-57.
Illouz, "Body Contouring by Lipolysis: A 5-Year Experience With Over 3000 Cases", Plast Reconstr Surg, 72: 691-597, 1983.
Kurita et al., "Influences of Centrifugation on Cells and Tissues in Liposuction Aspirates: Optimized Centrifugation for Lipotransfer and Cell Isolation", Plast. Reconstr. Surg., 121: 1033-1041, 2008.
Lv et al., "Concise Review: The Surface Markers and Identity of Human Mesenchymal Stem Cells", Stem Cells, 2014, 32: 1408-1419.
Rodbell, "Metabolism of Isolated Fat Cells", The Journal of Biological Chemistry, vol. 241, No. 1, pp. 130-139.
Shah et al., "A non-enzymatic method for isolating human adipose tissue-derived stromal stem cells", Cytotherapy, 2013; 15: 979-985.

* cited by examiner

MECHANICAL APPARATUS AND METHOD FOR ISOLATING STROMAL VASCULAR FRACTION

TECHNOLOGICAL FIELD

The invention generally concerns a non-enzymatic process for isolating stromal vascular fraction (SVF) of a unique constitution and apparatus for carrying out the process.

BACKGROUND

Adipose tissue represents an abundant and accessible source of adult stem cells capable of differentiating along multiple lineage pathways. Lipoaspirate obtained from adipose tissue has proven to serve as an accessible and rich source of various types of stem/progenitor cells having multipotent characteristics suitable for tissue engineering and regenerative medical applications [1].

Enzymatic digestion of the adipose tissue has been most commonly practiced for processing lipoaspirates. For example, the processing of lipoaspirate for isolation of adipose-derived stem/progenitor cells has previously been carried out by mincing rat fat pads, washing to remove contaminating hematopoietic cells and incubating the tissue fragments with collagenase to separate the floating population of mature adipocytes from the pelleted stromal vascular fraction (SVF) [2].

The development of liposuction surgery has simplified the procedure. During liposuction, a surgeon infuses the subcutaneous tissues with a saline solution containing anesthetic and/or epinephrine via a cannula and then removes both the liquid and tissue under suction to typically generate finely minced tissue fragments, the size of which depends on the dimensions of the cannula [3].

Thus, human adipose-derived stem/stromal cells can be readily isolated from biopsies and liposuction specimens [4]; can be derived from the liquid portion of liposuction aspirates with the use of an adherent column [5] and can also be isolated from human lipoaspirate samples by a non-enzymatic mechanical dissociation procedure [6].

While investigating quantitatively the effects of centrifugation on liposuction aspirates to optimize centrifugal conditions for fat transplantation and isolation of adipose-derived stem cells Kurita M, et al., suggested 1200× g as an optimized centrifugal force for obtaining good short- and long-term results in adipose transplantation [7].

Shah A, et al. described a non-enzymatic method of washing adipose tissue for isolating human adipose tissue-derived stromal stem cells [8].

Recently, a number of mechanical devices have been described for isolating adipose derived progenitor and/or stem cells from lipoaspirates.

US 2012/264213 [9] discloses a lipoaspirate extraction device which facilitate the collection and processing of mechanically released adipose derived progenitor and/or stem cells from fluid obtained during liposuction.

US 2013/034524 [10] discloses a device and method for extracting, separating and concentrating clinically useful regenerative cells from adipose tissue using a combination of mechanical disruption and filtration-centrifugation to obtain a highly enriched population of stem cells.

Alexander R W [11] reported on the differences in using microcannula lipoaspirates undergoing mechanical emulsification in order to pro-vide adult mature adipocyte lysis, preserving tissue stromal vascular fraction (tSVF) in small particle form which can be injected through small bore needles.

PUBLICATIONS

[1] Gimble J, *Circulation Research.* 2007, 100: 1249-1260;
[2] Rodbell M and Jones A B, *J Biol Chem,* 1966; 241: 140-142;
[3] Illouz Y G. *Plast Reconstr Surg,* 1983; 72: 591-597;
[4] Dubois S G, et al., *Methods Mol Biol,* 2008; 449:69-79;
[5] Kentaro Doi, et al., *Cytotherapy,* Vol. 16, Issue 3, 2014, Pages 381-391;
[6] Baptista L S, et al., *Cytotherapy,* 2009; 11(6):706-15;
[7] Kurita M, et al., *Plast Reconstr Surg.* 2008, 121(3):1033-41;
[8] Shah S, et al., *Cytotherapy,* 15(8), 2013, Pages 979-985
[9] US 2012/264213
[10] US 2013/034524
[11] Alexander R W, *Journal of Prolotherapy.* 2016; 8:e947-e960:
[12] Lv, F.-J., et al., *Stem cells.* 2014; 32:1408-1419.

General Description

The invention disclosed herein generally concerns an apparatus and process for isolation of stromal vascular fraction (SVF) following lipoaspiration.

More specifically, the present invention is directed to a mechanical method for isolating stromal cell fraction from fat tissue using a combination of mechanical disruption/dissociation, washing and centrifugation for obtaining an enriched population of stromal vascular fraction. The mechanical method is carried out in a closed single-use vessel or container or apparatus which is adapted to receive, manipulate and permit separation of the enriched cell population. The vessel is in a form of a "container assembly" (interchangeable herein with 'container'), in some embodiments being in a cylindrical side-wall shaped form, having a concave base, an upper ceiling portion and a planar bottom base enabling the container to stand unassisted on a flat surface. The vessel is configured to collect the adipocytes from a mammalian body and further adapted to promote retention of a cell pellet (e.g. following centrifugation of the container) in the lower portion of the container.

In some embodiments, the container assembly has a circular (e.g. snap-on, threaded) closing cap (lid) that acts to hermetically seal the container. The closing cap has multiple sealable inlets to allow insertion of tubes/cannulas into the contained unit. The sealable inlets are adapted to allow the insertion of various tubes and cannulas in accordance with a particular method of use (e.g. inserting a tube to let in washing solution; to attach the herein described aspiration tube and vacuum pump etc).

The closing cap of the container assembly is configured to allow the attachment of an electrical actuator that may be detachably connected (e.g. by a shaft/sleeve) to a mechanical tissue disruption device situated within the container assembly being adjacent to but having no contact with the concave base of the container.

The 'mechanical tissue disruption device' may be any device (e.g. closed contained) suitable for tissue disruption/dissociation which maintains cell viability throughout the disruption/dissociation process.

In some embodiments, the mechanical tissue disruption device comprises at least one rotatable blade or rotor.

In other embodiments, the mechanical tissue disruption device comprises grinding balls or beads (e.g. 0.5-2 mm diameter glass beads or zirconia/silica beads).

In accordance with the present invention, sterilization of the container assembly does not affect the sealing effect of the closing cap and/or inlets situated therein.

The "aspiration tube" (interchangeable herein with 'cannula') generally refers to a cannula that is commonly used for liposuction or any other medical procedure that involves the extraction of cells and/or tissue fragments from a bodily tissue (e.g. fat layer) of a mammal (e.g. by insertion through a small incision at the site of fat removal in the body to allow the adipocytes to be aspirated from the body via suction). Typically, the cannula constitutes a hollow tube blunted at the tip and having at least one opening (holes) at its tip. The cannula may be reusable (to allow multiple uses thereof) and may be sterilized by steam autoclave or by any other standard sterilization methods known in the art.

The cannula's hollow tube is configured to allow the passage of a mixture comprising liquid and fat tissue components (e.g. adipocytes, fragments of minced fat globules, torn fat cells) suctioned from a mammalian body into the cannula and directly into the container assembly through an inlet in the closing cap of the container assembly.

In accordance with the present invention, a vacuum pump is attached to the (e.g. closing cap or side wall) container to activate liposuction of adipose tissue into the container via the aspiration tube.

In some embodiments, the vacuum pump is a liposuction pump (e.g. any liposuction surgical suction pump known in the field of the art that can be used in accordance with the invention).

As used herein the term "adipose tissue" (interchangeable herein with 'adipocytes') generally refers to any type of cells and/or tissue fragments that can be isolated from adipose tissue and which can be used to isolate a stromal cell fraction (SVF) therefrom.

In accordance with the present invention, the SVF can be derived from both the fatty and fluid portions of liposuction aspirate and typically comprise a heterogeneous mix of multiple cell populations having different degree of maturity and function. Accordingly, the SVF is generally composed of a hematopoietic cell portion (e.g. granulocytes, monocytes and lymphocytes) together with pre-adipocytes, endothelial cells, pericytes, fibroblasts and stem progenitor cells.

In some embodiments, the SVF obtained in the method of the present invention is characterized by at least one of the following features:

The SVF is phenotypically identifiable as having a percentages of CD45+ cell of between about 40% and between about 91%;

The SVF is phenotypically identifiable as having a percentages of between about 5 and about 50 of CD45(−) CD31(−) CD34(+) and between about 3 and between about 40 of CD45(−) CD73(+) CD29(+) cells;

The SVF is phenotypically identifiable as having a percentages of between about 7 and about 40 of CD45(−) CD31(−) CD34(+) and between about 6 and about 30 of CD45(−) CD73(+) CD29(+) cells;

The SVF is phenotypically identifiable as having a percentages of between about 2 and between about 15 of CD45(−) CD31(−) gate of monocytes (+) CD34 (+) cells;

The SVF is phenotypically identifiable as having a percentages of between about 4 and between about 10 of CD45(−) CD31(−) gate of monocytes (+) CD34 (+) cells;

The SFV yield of nucleated cells is higher by at least 3 fold then that obtained in the herein described wash only method;

The quantity of cells per 1 ml of lipoaspirate after cell culturing for a period of between 7 and 14 days is higher by at least 15 fold as compared with that obtained in the wash only method, as further described below;

The SVF contains a higher percentage of mesenchymal progenitor stem cells as compared to that obtained in the wash only method, as measured by the differentiation capacity of the cells and by specific stem cell markers and physical properties as identified by flow cytometry;

The SVF is injectable (e.g. into a mammalian tissue for) via very small needles having a gauge number of between 33 gauge and 7 Gauge.

In some embodiments, the SVF obtained in the method of the present invention is characterized as having a percentages of between about 7 and about 40 of CD45(−) CD31(−) CD34(+) and between about 6 and about 30 of CD45(−) CD73(+) CD29(+) cells; and/or as having a percentages of between about 4 and about 10 of CD45(−) CD31(−) gate of monocytes (+) CD34 (+) cells.

In some embodiments, the SVF is phenotypically identifiable as having a percentages of between about 5 and about 50 of CD45(−) CD31(−) CD34(+) and between about 3 and between about 40 of CD45(−) CD73(+) CD29(+) cells. In some embodiments, the SVF is phenotypically identifiable as having a percentages of between about 7 and about 40 of CD45(−) CD31(−) CD34(+) and between about 6 and about 30 of CD45(−) CD73(+) CD29(+) cells.

In some embodiments, the SVF is phenotypically identifiable as having a percentages of between about 2 and between about 15 of CD45(−) CD31(−) gate of monocytes (+) CD34 (+) cells. In some embodiments, the SVF is phenotypically identifiable as having a percentages of between about 4 and between about 10 of CD45(−) CD31(−) gate of monocytes (+) CD34 (+) cells.

In some embodiments, the diameter of the aspiration cannula is between about 0.5 mm and between about 10 mm.

In other embodiments, the diameter of the aspiration cannula is between about 2 mm and between about 6 mm, or between about 3 mm and about 5 mm.

The cannula of the present invention may have various types of tips at its distal end to optimize attachment and insertion into the fat layer for harvesting of adipocytes. As the skilled artesian would readily realize, the optimal size (e.g. diameter, length) and type of material of the cannula is dictated based on various parameters associated with the condition of the patient, the specific requirements of the physician performing the liposuction, the intended use of the harvested adipocytes, etc.

As a person skilled in the art would realize, the aspiration (liposuction) process may partially rupture the aspirated adipose tissue (e.g. into fat globules) due to the shear forces affected during suction and passage through the aspiration tube. Accordingly, the adipocytes collected into the contained may be already partially disrupted. Once the adipocytes are collected in the container assembly, mechanical disruption of the harvested adipocytes is carried out in either in the fluid aspirated during liposuction (e.g. composed primarily of lipoaspirate in physiological solution but which may also contain remnants of local anesthetic substance such as lidocaine and epinephrine) or in the washing solution or in the isolated lipoaspirate that was separated from any added solutions using the mechanical tissue disruption device controlled by an electrical actuator being external and detachably connected to the closing cap of the container. The mechanical tissue disruption device (typically comprising at least one rotor or blade to affect a rotational force) is configured to be lowered and retracted to and from the concave bottom of the container and to be locked in place (e.g. during mechanical disruption of the adipocytes).

The rotor speed of the mechanical tissue disruption device (measured in rates per minute [RPM]) is adapted to maintain the viability of stromal vascular fraction cells aspirated from the fat layer of the body, e.g. by producing a homogenous single cell suspension, preserving cell integrity and preventing foaming and protein denaturation.

In some embodiments, the rotor rotates at between about 500 RPM and about 8,000 RPM. In some embodiments, the rotor rotates at between about 1,000 and 6,000 RPM. In some embodiments, the rotor rotates at between about 1,100 and 1,500 RPM.

The mechanical disruption utilized in accordance with the present invention does not necessitate enzymatic digestion at any stage of the harvesting and manipulation of the tissue and cells.

In some embodiments, the mechanical disruption is carried out in the lipoaspirate solution without the addition of a washing solution. In accordance with such embodiments, upon completion of the mechanical disruption, the mechanically disrupted lipoaspirate may be washed, at least once, as described herein.

In other embodiments, prior to mechanical disruption of the harvested lipoaspirate, the lipoaspirate is washed extensively (e.g. to remove contaminating blood) using a washing solution (e.g. saline or any other suitable physiological solution at a temperature of between about 4 degrees Celsius and between about 37 degrees Celsius) transferred through at least one inlet in the closing cap of the container, wherein after each washing step, the container in transferred into a centrifuge adapted to receive the container and is centrifuged at a sufficient force and for a sufficient period of time to form a supernatant and a (e.g. soft) cell pellet at the bottom (concave) portion of the container. According to such embodiments, the mechanical disruption is carried out in the washing solution and may be carried out once or repeated at least one more time after each washing step.

Following mechanical disruption, the lipoaspirate may be washed again, at least once, as described herein.

In some embodiments, the washing solution is funneled (e.g. continuously) into the container during the mechanical disruption of the harvested lipoaspirate.

In other embodiments, the washing solution is funneled into the container before the lipoaspirate is suctioned into the container and then following each step of centrifugation.

As readily recognized by the person of skill in the art, each washing step described herein is followed by centrifugation wherein immediately following centrifugation, the washing solution (i.e. supernatant) is gently aspirated. The washing may be repeated one or more times, wherein centrifugation is performed after each washing step and wherein the washing solution is aspirated out of the vessel and a new solution is introduced.

In some embodiments, the washing solution further contains (e.g. for the purpose of enriching a specific cell fraction and/or to aid fractionation of the adipocytes) at least one additional reagent. Some non-limiting examples of such reagents include a cell specific antibody, a buffering agent, a sugar based density gradient (e.g. sucrose, manose, ficoll, Dextran sulfate), a none-sugar density gradient (e.g. percoll, percoll plus, Histopaque®) an antibody mediated magnetic cell sorting solution, non-magnetic antibody mediated cell sorting solution (not magnetic).

In accordance with the present invention, the centrifugation acts to separate the cells (e.g. stromal vascular fraction) from the floating population of cells (e.g. mature adipocytes).

In some embodiments, the container may be centrifuged (e.g. to separate SVF cells from floating adipocytes) at between about 200× g about and between about 1,500×g, or at between about 250× g and between about 500× g.

Following each centrifugation of the container, the container is taken out of the centrifuge and the cell pellet is gently aspirated using an aspirating needle or any mechanical means suitable to withdraw the pellet from within the vessel.

In some embodiments, following at least one washing step, the cell pellet is gently aspirated after phase separation occurs without performing centrifugation.

In some embodiments, the cell pellet is transferred through a strainer (e.g. having a mesh size of between about 40 μM and between about 200 μM) before counting nucleated cells.

In some embodiments, the cell pellet is further processed to enrich for a specific desirable cell population (e.g. using fluorescence-activated cell sorting (FACS)-based techniques or any other suitable cell enrichment method known to the skilled artesian).

The skilled artesian would readily recognize that any of the procedures carried out during the mechanical disruption method (e.g. disruption, washing, centrifugation) can be carried out at between about 4 degrees Celsius and between about 37 degrees Celsius depending on various parameters associated with the method of the invention (e.g. type of adipose tissue, rotor speed, rotor type, solution to adipose tissue ratio etc.) which are known to the skilled artesian.

In some embodiments, the method of the invention involves the addition of saline (e.g. pre-warmed to about 37 degrees Celsius) to the lipoaspirate, following which a mechanical disruption of the fat/saline mixture is carried out (e.g. at room temperature) and the mechanically disrupted fat (with saline) is centrifuged and transferred trough a strained or filter.

Thus, in some aspects, the invention provides a container or a vessel as described herein.

In another of its aspects the present invention provides a method for enriching a cell population from a mammalian adipose tissue, the method comprising:
  aspirating adipose tissue into a container assembly (e.g., using an aspiration tube having a proximal end detachably connected to the container unit and a distal end inserted into at least one cavity of a mammalian body);
  mechanically disrupting/rupturing the adipose tissue in the container assembly (e.g., using a mechanical tissue disruption device to obtain a cell suspension, wherein the disruption does not utilize an enzyme);
  washing the suspension of cells within the container assembly; and
  transferring the container assembly into a centrifuge and centrifuging the container assembly to thereby obtain a cell pellet.

In some embodiments, the method further comprises a step of extracting the cell pellet from within the container assembly to obtain an enriched cell population.

In some embodiments, the enriched cell population obtained is an SVF cell fraction characterized by at least one of the following features:

- The SVF is phenotypically identifiable as having a percentages of CD45+ cell of between about 40% and between about 91%;
- The SVF is phenotypically identifiable as having a percentages of between about 5 and about 50 of CD45(−) CD31(−) CD34(+) and between about 3 and between about 40 of CD45(−) CD73(+) CD29(+) cells;
- The SVF is phenotypically identifiable as having a percentages of between about 7 and about 40 of CD45(−) CD31(−) CD34(+) and between about 6 and about 30 of CD45(−) CD73(+) CD29(+) cells;
- The SVF is phenotypically identifiable as having a percentages of between about 2 and between about 15 of CD45(−) CD31(−) gate of monocytes (+) CD34 (+) cells;
- The SVF is phenotypically identifiable as having a percentages of between about 4 and between about 10 of CD45(−) CD31(−) gate of monocytes (+) CD34 (+) cells;
- The SFV yield of nucleated cells is higher by at least 3 fold then that obtained in the herein described wash only method;
- The quantity of cells per 1 ml of lipoaspirate after cell culturing for a period of between 7 and 14 days is higher by at least 15 fold as compared with that obtained in the wash only method, as further described below;
- The SVF contains a higher percentage of mesenchymal progenitor stem cells as compared to that obtained in the wash only method, as measured by the differentiation capacity of the cells and by specific stem cell markers and physical properties as identified by flow cytometry.
- The SVF is injectable (e.g. into a mammalian tissue for) via very small needles having a gauge number of between 33 gauge and 7 Gauge.

In other embodiments, the method comprises a step of isolating the fat from which the SVF fraction was obtained and using same in a method of cosmetic or therapeutic utility.

The invention further provides a SVF fraction characterized by any one of:

- The SVF is phenotypically identifiable as having a percentages of CD45+ cell of between about 40% and between about 91%;
- The SVF is phenotypically identifiable as having a percentages of between about 5 and about 50 of CD45(−) CD31(−) CD34(+) and between about 3 and between about 40 of CD45(−) CD73(+) CD29(+) cells;
- The SVF is phenotypically identifiable as having a percentages of between about 7 and about 40 of CD45(−) CD31(−) CD34(+) and between about 6 and about 30 of CD45(−) CD73(+) CD29(+) cells;
- The SVF is phenotypically identifiable as having a percentages of between about 2 and between about 15 of CD45(−) CD31(−) gate of monocytes (+) CD34 (+) cells;
- The SVF is phenotypically identifiable as having a percentages of between about 4 and between about 10 of CD45(−) CD31(−) gate of monocytes (+) CD34 (+) cells;
- The SFV yield of nucleated cells is higher by at least 3 fold then that obtained in the herein described wash only method;
- The quantity of cells per 1 ml of lipoaspirate after cell culturing for a period of between 7 and 14 days is higher by at least 15 fold as compared with that obtained in the wash only method, as further described below;
- The SVF contains a higher percentage of mesenchymal progenitor stem cells as compared to that obtained in the wash only method, as measured by the differentiation capacity of the cells and by specific stem cell markers and physical properties as identified by flow cytometry.
- The SVF is injectable (e.g. into a mammalian tissue for) via very small needles having a gauge number of between 33 gauge and 7 Gauge.

In some embodiments, the SVF fraction is produced according to a method of the invention.

In some embodiments, the SVF fraction, whether or not produced by a method of the invention, may be used in medicine.

The invention further provides a process and a device for the mechanical isolation of stromal vascular fraction (SVF) cells by pressure filtration. The device comprises two spreadable containers, separable by a shutter having a closed position and an open position. When in a closed position a lipoaspirate is transferred into a top container and is permitted to settle.

Subsequently, the shutter is turned to the "on" position and fat is permitted to pass through the metal mesh or filter separating between the two containers, by inducing pressure down the plunger.

Once all fat and fluid were passed through the mesh into the bottom container the shutter is turned into a closed position. After separating the bottom container the fat remains sterile because the top end is closed by the shutter.

The separated bottom container is centrifuged and SVF cells are concentrated at the bottom of the container and may be separated therefrom.

The invention further provides an isolated SVF fraction of adipose tissue cells, the fraction characterized by at least one of the following features:

1. Having an SVF cell yield similar to the one gained by collagenase (e.g., Collagenase type I) isolation;
2. Having a culture expansion capability similar to that obtained by the collagenase isolation method after both 7 and 14 days of culture;
3. Having a differentiation capability to both bone and fat;
4. Having a mesenchymal stem cells surface marker expression phenotype after passage 1 in culture;
5. Having between about 4% and between about 10% of CD45(−) gate of monocyte (+) CD34 (+) cells.

In still another one of its aspects, the present invention provides an isolated SVF fraction, obtained by the method and device of the invention, for use in regenerative medicine and in wound healing; for tissue (e.g. fat, bone, cartilage, skin, heart, liver, kidney, brain) regeneration and replacement (e.g. following trauma or in aesthetic surgery) and for immunoregulation purposes (e.g. in graft-versus-host disease, and other autoimmune diseases and for prevention of transplant rejection).

In some embodiments, the isolated SVF fraction can be used in combination with autologous fat for improved fat survival and blood vessels regeneration.

In accordance with the present invention, the herein defined isolated SVF fraction may be used either immediately after its isolation or following culturing (e.g. as adipose derived mesenchymal stem cells).

In another one of its aspects, the present invention provides use of an isolated SVF fraction, as disclosed herein, in regenerative medicine or in wound healing; for tissue (e.g. fat, bone, cartilage, skin, heart, liver, kidney, brain) regeneration and replacement (e.g. following trauma or in aesthetic surgery), for immunoregulation purposes (e.g. in graft-versus-host disease, and other autoimmune diseases and for prevention of transplant rejection), or for any other medicinal purpose as may be known to a medical professional or practitioner.

The invention further provides a method of using an SVF fraction according to the invention, the method comprising a step of obtaining an SVF fraction as disclosed herein and using said fraction as known in the art. In some embodiments, the method is selected from methods of regenerative medicine, methods for inducing wound healing; methods for tissue (e.g. fat, bone, cartilage, skin, heart, liver, kidney, brain) regeneration and replacement (e.g. following trauma or in aesthetic surgery) and methods for immunoregulation (e.g. in graft-versus-host disease, and other autoimmune diseases and for prevention of transplant rejection).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 5A depicts all nucleated cells and FIG. 5B depicts CD45(−) only cells.

DETAILED DESCRIPTION OF EMBODIMENTS

The present invention is directed to a mechanical method for isolating adipocytes from fat tissue, using a combination of mechanical disruption, washing and centrifugation for obtaining an enriched population of stromal vascular fraction.

In order to have a better understanding of the invention, the reader is now directed to the figures.

Figure 1:
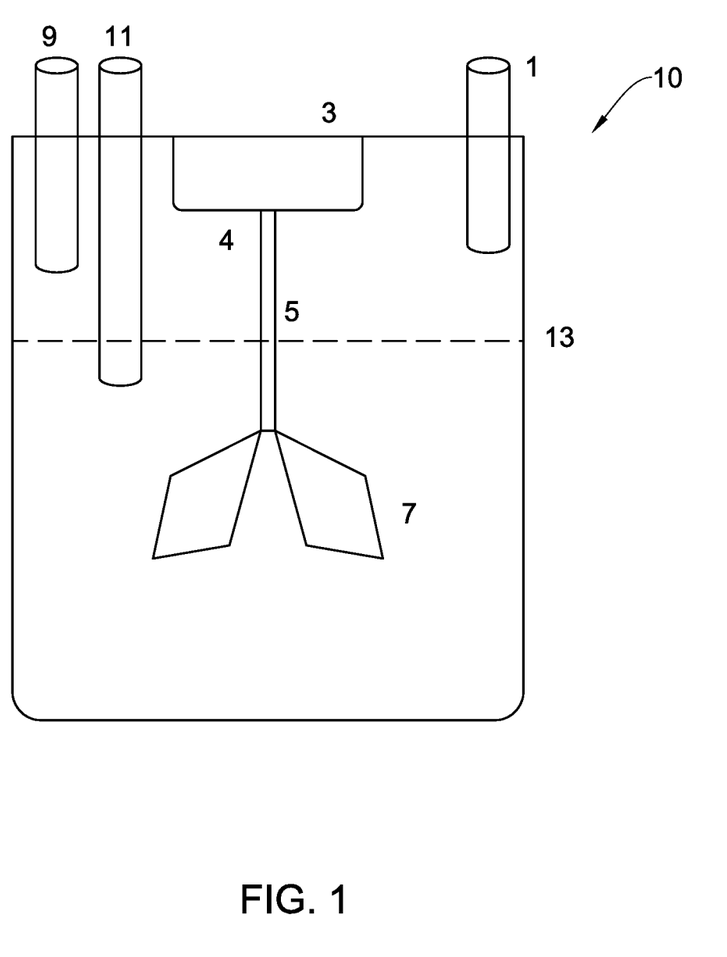
FIG. 1 depicts a device for collecting adipocytes according to some embodiments of the invention.

Reference is first made to FIG. 1 which provides an exemplary embodiment of a device 10 having an inlet 1 communicating with the interior of said device and adapted to sealably and detachably engage a cannula for introducing cells into the device, a sealable and detachable closing cap 3, a proximal mount 4 for a rotor shaft 5 and a rotor 7 attached thereto.

The closing cap 3 of the device 10 further includes two additional inlets 9 and 11 to let in a washing solution (e.g. normal saline, ringer's solution, lactated ringer's solution, hanks' balanced salt solution and any combination thereof) through cannulas inserted therethrough. The solution or liquid or fat level is typically maintained at or below level 13.

Figure 2:
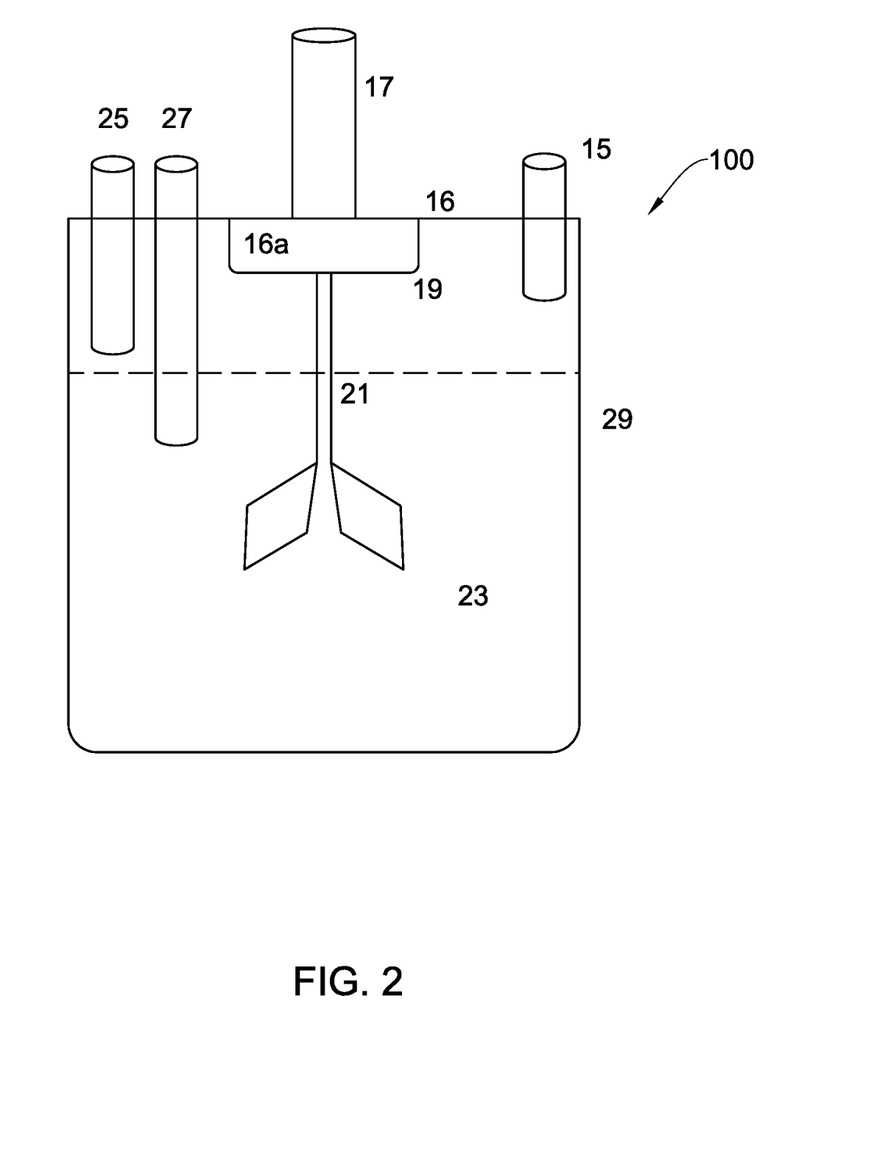
FIG. 2 depicts a device for isolating SVF cells according to some embodiments of the invention.

Turning to device 100, shown in FIG. 2, an electrical actuator external to the closing cap 16 is depicted, said actuator being detachably connected by a shaft 21 to the rotor through a sealable opening 16a in the closing cap. Features 25, 27, 15, 16 and 29 are equivalent to features 9, 11, 1, 3 and 13 shown in FIG. 1, respectively.

Figure 3:
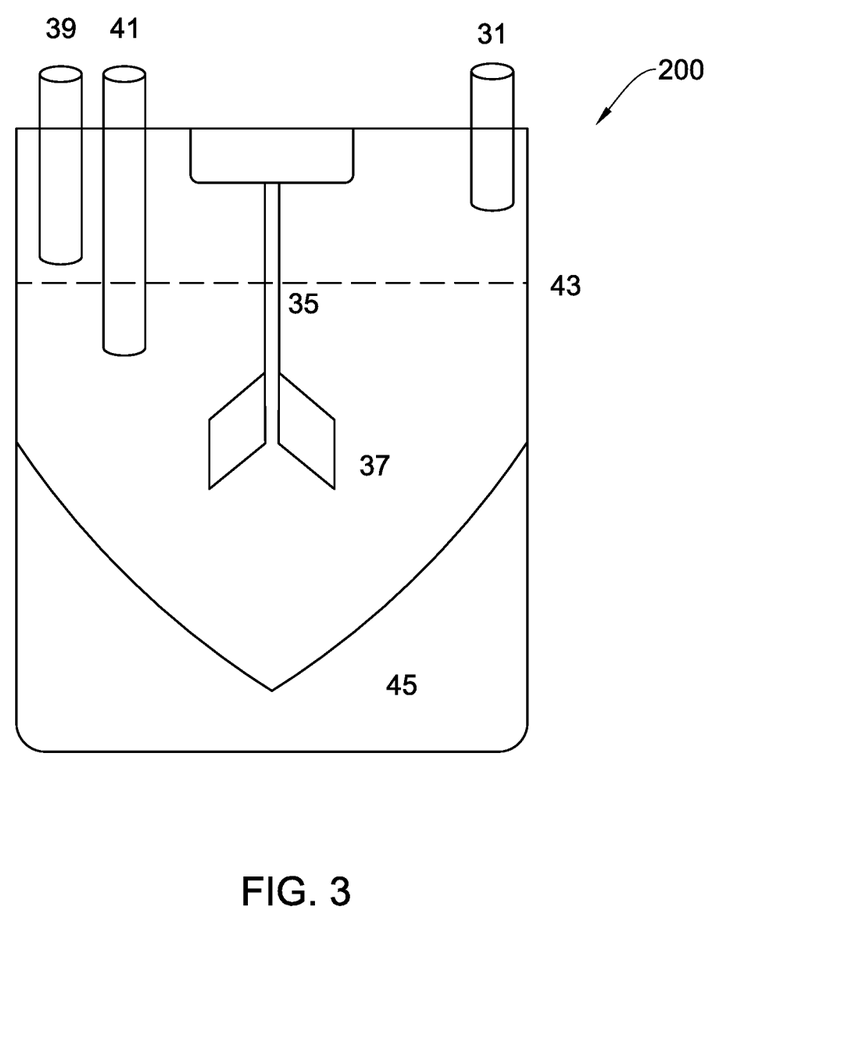
FIG. 3 depicts a device for isolating SVF cells according to some embodiments of the invention.

Additional reference is made to device 200, shown in FIG. 3, which further depicts the concave base 45 of said device adapted for collection of the cells. Features 39, 41, 31, and 43 are equivalent to features 9, 11, 1, and 13 shown in FIG. 1, respectively.

It is appreciated that device 10, 100 or 200 can be of a cylindrical, rectangular, trapezoid shape and any other known suitable geometry in the art and can be made from any inert, transparent or opaque, stable and sealable (e.g. under vacuum and using a hermetically sealed closing cap) material suitable to collect cells and maintain the sterility and viability thereof such as a thermoplastic polymer (e.g. polypropylene), a synthetic aromatic polymer (polystyrene) and a metal (e.g. aluminum).

Regardless of the material and shape of the device, the volume of the device may be between 0.05 liter and 2 liters.

The actuator may be motor-driven (e.g. electrical) or manually operated.

The cannula may be made from any flexible non-reactive material (e.g. silicone, polyvinyl chloride).

Example 1

Fat was isolated from thighs of a 50 years female by liposuction. The highest body mass index (BMI) previously measured was 52.7 and from a stable BMI of 33.9 was measured over a period 5 years. Fat was kept at 4 degrees Celsius overnight and processed at the next morning.

Isolation of Cells from Fat by Collagenase I (Comparative System):

Lipoaspirate fat (25 ml) was washed by adding 25 ml saline followed by thorough mixing and centrifugation at 260×g for 5 minutes. Washed fat (in 10 ml portions) was mixed with 0.75 ml of 5 mg/ml collagenase I suspended in DMEM. The lipoaspirate/collagenase mixture was rotated for 1 hour at 37 degrees Celsius. Following the enzymatic digestion the fat/collagenase mixture was neutralized by 1/1 volume of DMEM with 10% FCS, transferred through a 100 µM strainer and followed by 15 minutes of centrifugation at 328×g. Sedimented stromal vascular fraction (SVF) cells were separated from floating adipocytes, transferred through a 100 µM strainer and nucleated cells were counted using 3% Acetic Acid with Methylene Blue (Stem cells technologies, Vancouver, Canada).

Mechanical Isolation Cells from Fat:

Lipoaspirate fat (100 ml) was washed by addition of 100 ml saline followed by thorough mixing and centrifugation at 328×g for 10 minutes. Washed fat (100 ml) was taken into an ATL-604 food processor (Gold-line, Israel) and 100 ml of saline was added. The fat/saline mixture was mechanically disrupted at 1300 RPM for 15 seconds at room temperature. Mechanically disrupted fat (with saline) was centrifuged at 328× g for 10 minutes. Sedimented SVF cells were separated from floating adipocytes and transferred through a 100 µM strainer. Nucleated cells were counted using 3% Acetic Acid with Methylene Blue (Stem cells technologies, Vancouver, Canada).

Isolation of Cells from Fat by Thorough Mixing and Centrifugation:

Lipoaspirate fat (25 ml) was washed by addition of 25 ml saline followed by thorough mixing and centrifugation at 328×g for 10 minutes. Sedimented SVF cells were separated from floating adipocytes. Nucleated cells were counted using 3% Acetic Acid with Methylene Blue (Stem cells technologies, Vancouver, Canada).

Cell Culturing:

Following their isolation and cell counting, SVF cells from all 3 isolation protocols (collagenase, mechanical and wash), were seeded at a concentration of $5 \times 10^5$ cells/well of a 6 well plate and cultured for 7 days. Cells were cultured in high glucose Dulbecco's modified Eagle's medium (DMEM; Gibco, Paisley, Scotland, UK) supplemented with 10% FCS (Thermo Scientific HyClone, Tauranaga, New Zealand), 60 µg/mL penicillin, 100 µg/mL streptomycin, 50 µg/mL kanamycin, sodium pyruvate (1 mM), L-glutamine (2 mM) and non-essential amino acids. Cultures were propagated at 37° C. in a 10% $CO_2$ atmosphere. Medium was changed 72 hours after cell seeding. After seven days in culture, cells were harvested by trypsin and counted.

Results:

As can be seen in Table 1, similar quantities of nucleated cells were isolated from fat using collagenase and mechanical cell isolation methods. In spite of vigorous washing, cell isolation without enzymatic or mechanical disruption of fat resulted in significantly lower quantities of cells.

Additionally, culturing for 7 days of SVF cells in identical quantities resulted in significantly higher numbers of stromal cells when collagenase and mechanical isolated cells were used compared to cells that were isolated by washing only (Table 1). Importantly, similarly to a previous report [8] the cell yield per 1 ml of fat following culture was 30 fold higher in enzymatically isolated cells compared to cells that were isolated by washing only ($1.08 \times 10^5$ cells/1 ml fat (enzymatic) and $0.036 \times 10^5$ cells/1 ml fat (wash). In contrast, cell yield following mechanical cell isolation and culture was similar to that obtained following enzymatic isolation ($1.08 \times 10^5$ cells/1 ml fat (enzymatic) and $0.656 \times 10^5$ cells/1 ml fat (mechanical).

TABLE 1

| Isolation method | Nucleated cells per 1 ml fat (lipoaspirate) | Dead cells (percent) | Cells/well of a 6 well plate (after 7 days in culture) | Cultured cells per 1 ml fat (after 7 days in culture) |
|---|---|---|---|---|
| Collagenase | $5.4 \times 10^5$ | 2.5% | $1 \times 10^5$ | $1.08 \times 10^5$ |
| Mechanical disruption | $4.1 \times 10^5$ | 0.9% | $0.8 \times 10^5$ | $0.656 \times 10^5$ |
| Wash | $1.4 \times 10^5$ | 0.2% | $0.13 \times 10^5$ | $0.036 \times 10^5$ |

Example 2

Fat was isolated from the abdominal wall, hips and back of a 46 years male by liposuction. The highest BMI previously measured was 62 and was later measure to be at a stable BMI=31 for a period of over a year. Fat was kept at 4 degrees overnight and processed at the next morning.

Isolation of Cells from Fat by Collagenase I (Comparative System):

Lipoaspirate fat (80 ml) was washed by addition of 80 ml saline followed by thorough mixing and centrifugation at 260×g for 5 minutes. Washed fat (in 10 ml portions) was mixed with 0.75 ml of 5 mg/ml collagenase I suspended in DMEM. The lipoaspirate/collagenase mixture was rotated for 1 hour at 37 degrees. Following the enzymatic digestion the fat/collagenase mixture was neutralized by 1/1 volume of DMEM with 10% FCS, followed by 15 minutes of centrifugation in 328× g. Sedimented stromal vascular fraction (SVF) cells were separated from floating adipocytes transferred through 100 µM strainer and, nucleated cells were counted using 3% Acetic Acid with Methylene Blue (Stem cells technologies, Vancouver, Canada).

Mechanical Isolation Cells from Fat:

Lipoaspirate fat (25 ml) was washed by addition of 25 ml saline followed by thorough mixing and centrifugation 260× g for 5 minutes. Washed fat (25 ml) was taken into a Philips HR1611 food processor and 25 ml of saline was added. The fat/saline mixture was mechanically disrupted at 5240 RPM for 8 seconds at room temperature. Mechanically disrupted fat (with saline) was centrifuged at 328×g for 10 minutes. Sedimented SVF cells were separated from floating adipocytes and transferred through 100 µM strainer. Nucleated cells were counted using 3% Acetic Acid with Methylene Blue (Stem cells technologies, Vancouver, Canada).

Cell Culturing:

Following their isolation and cell counting, SVF cells from the two isolation protocols (collagenase and mechanical), were seeded at a concentration of $5 \times 10^5$ cells/6 cm plate and cultured for 14 days. Cells were cultured in high glucose Dulbecco's modified Eagle's medium (DMEM; Gibco, Paisley, Scotland, UK) supplemented with 10% FCS (Thermo Scientific HyClone, Tauranaga, New Zealand), 60 µg/1 mL penicillin, 100 µg/1 mL streptomycin, 50 µg/1 mL kanamycin, sodium pyruvate (1 mM), L-glutamine (2 mM) and non-essential amino acids. Cultures were propagated at 37° C. in a 10% $CO_2$ atmosphere. Medium was changed 72 hours after cell seeding and then every 3 days. After 14 days in culture cells were harvested by trypsin and counted.

Cell Surface Marker Staining:

Following cell harvest cells were stained by a panel of cell markers including: anti human CD45 (BD horizon), anti human CD31 (eBioscience), anti human CD105, anti human CD34, anti human CD29, anti human CD235α, anti human CD73 (Biolegend, San Diego, CA, USA) and live/dead-vivid dye (Invitrogen Molecular Probes, Eugene, OR, USA). Labeled cells were analyzed using a BD FACS Canto II flow cytometer (Becton Dickinson, San Jose, CA, USA). Data analysis was performed by the flow-Jo software (Tree star, Ashland, OR USA).

Results:

In accordance with example 2, similar quantities of cells were isolated from fat using collagenase digestion or mechanical isolation (Table 2).

Additionally, culturing of SVF cells for 14 days resulted in the expansion of similar numbers of stromal cells when collagenase and mechanical isolated cells were used (Table 2).

Evaluation of the surface marker expression pattern of cultured stromal cells at passage 0 after 14 days of tissue expansion revealed the expected expression pattern in both the enzymatically and mechanically isolated cells. The pattern included a negligible percent of CD45 (+) hematopoietic cells and high expression of mesenchymal stem cells markers (100% CD73 expression and >90% expression of CD29 and CD105) in most of the cultured cells (Table 3).

Thus, mechanical isolation of SVF cells from fat allows the extraction of high quantities of nucleated cells similarly to enzymatic extraction. In addition, mechanically isolated cells harbor similar properties to enzymatically isolated cells as they produce similar quantities of cells following 14 days propagation in culture with a similar surface marker expression pattern.

TABLE 2

| Isolation method | Nucleated cells/1 ml lipoaspirate | Dead cells (percent) | Cells/6 cm plate (after 14 days in culture) |
| --- | --- | --- | --- |
| Collagenase | $2.3 \times 10^5$ | 17% | $6.7 \times 10^5$ |
| Mechanical disruption | $1.5 \times 10^5$ | 3% | $5.8 \times 10^5$ |

TABLE 3

| Surface markers expression | Collagenase dissociation P0 | Mechanical dissociation P0 |
| --- | --- | --- |
| CD45(+) | 0.1% | 0.4% |
| CD31(+) CD34(−) | 1% | 0.6% |
| CD31(−) CD34(+) | 0.5% | 0.9% |
| CD29(+) CD105(+) | 95.6% | 93% |
| CD73(+) | 100% | 100% |

Example 3

Fat was isolated from the abdominal wall and hips of a 60 years female by liposuction. The highest BMI previously measured was 40 and was followed by a measurement of a stable BMI 29 for a period of over a year. Fat was kept at 4 degrees Celsius overnight and processed at the next morning.

SVF cells were isolated from Lipoaspirate fat as was previously described in example 2 either by mechanical dissociation or by washing. Isolated cells were stained by the indicated markers and the proportion of cells positive for each marker was determined from the total population excluding dead cells and erythrocytes.

Results:

As can be seen, the proportion of CD45(+) hematopoietic cells was much higher in cells that were isolated by washing (91%) compared to mechanically isolated cells (29%) (Table 4). The increased proportion of CD45(+) in cells that were isolated by washing is in accordance with a previous report that found 81% of CD45(+) cells using similar extraction protocols. In spite of the difficulty to identify mesenchymal stem cell progenitors by specific surface markers [12], it is generally accepted that these cells do not originate from the CD45(+) population. Thus, the increased proportion of CD45(+) cells in cells isolated by washing can explain their poor culture expansion capacity compared to both mechanically and enzymatically isolated cells (Table 1).

TABLE 4

|  | Mechanical dissociation | Wash |
| --- | --- | --- |
| CD45 (+) | 29% | 91% |
| CD31(+) | 8.2% | 19% |
| CD34(+) | 8.2% | 9% |

Example 4

Figure 4A:
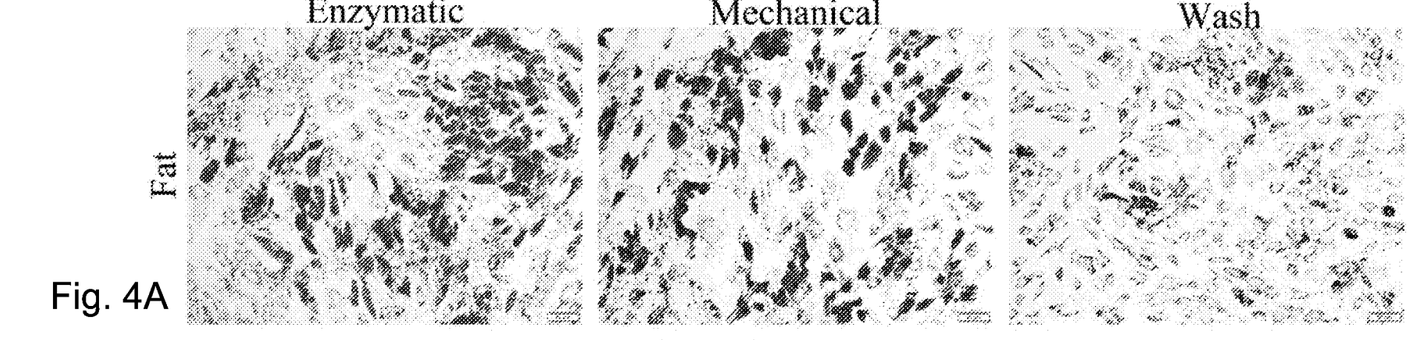
FIGS. 4A-B depict mechanically and enzymatically isolated SVF cells which display a similar fat (FIG. 4A) and bone (FIG. 4B) differentiation potential. Adipose derived stem cells isolated from fat using enzymatic, mechanical or wash techniques were incubated in a bone differentiation medium or with a fat differentiation medium or with control medium for 3 weeks. The cells were then stained for bone with alizarin red or for fat with Oil red O. Human. ASC differentiation into bone and fat is shown.
Figure 4B:
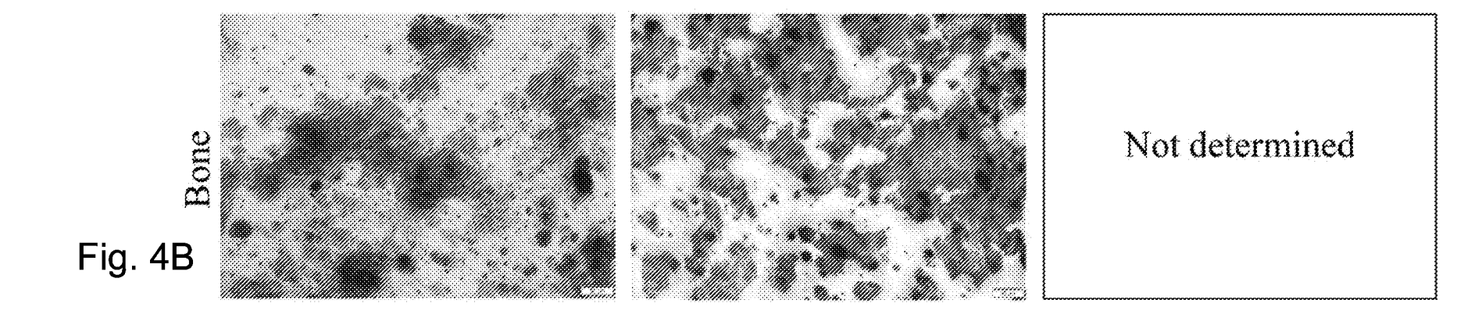

Differentiation Potential:

The multipotent potential of adipose derived stem cells isolated by enzymatic, mechanical and washing techniques was examined. As can be seen in FIG. 4, cultured cells that were isolated both by mechanical and enzymatic isolations demonstrated similar differentiation potential to both fat (FIG. 4A) and bone (FIG. 4B). Cells isolated by washing displayed a reduced fat differentiation potential compared to both mechanically and enzymatically isolated cells. Thus, mechanically isolated cells demonstrate comparable multipotent properties to enzymatically isolated cells and superior multipotency as compared to cells isolated by washing.

Furthermore, subcutaneous fat was isolated from the stomach of a 58 years female by liposuction. The highest body mass index (BMI) previously measured was and from a stable BMI of was measured over a period 5 years. Fat was kept at 4 degrees Celsius overnight and processed at the next morning.

Isolation of Cells from Fat by Collagenase I (Comparative System):

Lipoaspirate fat (25 ml) was mixed with 0.75 ml of 5 mg/ml collagenase I suspended in DMEM. The lipoaspirate/collagenase mixture was rotated for 1 hour at 37 degrees Celsius. Following the enzymatic digestion the fat/collagenase mixture was neutralized by 1/1 volume of DMEM with 10% FCS, transferred through a 100 μM strainer and followed by 15 minutes of centrifugation at 400×g. Sedimented stromal vascular fraction (SVF) cells were separated from floating adipocytes, transferred through a 100 μM strainer and nucleated cells were counted using 3% Acetic Acid with Methylene Blue (Stem cells technologies, Vancouver, Canada).

Mechanical Isolation Cells from Fat:

Lipoaspirate fat (100 ml), warmed to 37 degrees Celsius was taken into an ATL-604 food processor (Gold-line, Israel) and 100 ml of saline which was pre-warmed to 37 degrees Celsius was added. The fat/saline mixture was mechanically disrupted at 1300 RPM for 15 seconds at room temperature. Mechanically disrupted fat (with saline) was centrifuged at 400×g for 15 minutes. Sedimented SVF cells were separated from floating adipocytes and transferred through a 100 μM strainer. Nucleated cells were counted using 3% Acetic Acid with Methylene Blue (Stem cells technologies, Vancouver, Canada).

Isolation of Cells from Fat by Thorough Mixing and Centrifugation:

Lipoaspirate fat (10 ml), warmed to 37 degrees Celsius was washed by addition of 25 ml saline warmed to 37 degrees Celsius followed by thorough mixing and centrifugation at 400×g for 15 minutes. Sedimented SVF cells were separated from floating adipocytes. Nucleated cells were counted using 3% Acetic Acid with Methylene Blue (Stem cells technologies, Vancouver, Canada).

Cell Culturing:

Following their isolation and cell counting, SVF cells from all 3 isolation protocols (collagenase, mechanical and wash), were seeded at a concentration of 0.075 λ$10^6$ cells/well of a 6 well plate and cultured for 7 days. Cells were cultured in high glucose Dulbecco's modified Eagle's medium (DMEM; Gibco, Paisley, Scotland, UK) supplemented with 10% FCS (Thermo Scientific HyClone, Tauranaga, New Zealand), 60 μg/mL penicillin, 100 μg/mL streptomycin, 50 μg/mL kanamycin, sodium pyruvate (1 mM), L-glutamine (2 mM) and non-essential amino acids. Cultures were propagated at 37° C. in a 10% $CO_2$ atmosphere. Medium was changed 72 hours after cell seeding. After seven days in culture cells were harvested by trypsin and counted.

Cell Surface Marker Staining:

Following cell harvest cells were stained by a panel of cell markers including: anti human CD45 (BD horizon), anti-human CD31 (eBioscience), anti-human CD105, anti-human CD34, anti-human CD29, anti-human CD235α, anti-human CD73 (Biolegend, San Diego, CA, USA) and live/dead-vivid dye (Invitrogen Molecular Probes, Eugene, OR, USA). Labeled cells were analyzed using a BD FACS Canto II flow cytometer (Becton Dickinson, San Jose, CA, USA). Data analysis was performed by the flow-Jo software (Tree star, Ashland, OR USA). The gradual gating strategy isolated a distinct population containing only singlets and live cells (determined by low ViViD staining (an amine reactive viability dye while discarding RBCs (specific staining of RBC). Gating for CD45 (−) cells was than performed to eliminate CD45-positive immune cells. An additional gating of CD45-negative cells was performed to define the populations positive for CD31, CD34, CD73 and CD29. It is widely accepted that plotting forward scatter (FSC) data against side scatter data can reveal morphology information about a peripheral blood sample. FSC data plotted on the x-axis allows for size distinction with smaller lymphocytes appearing to the far left, while SSC data (y-axis) makes differentiating between the comparably sized monocytes and neutrophils possible based on cell granularity. Using the same parameters and whole blood as a positive control a distinct population was identified within the SVF having the same characteristic as monocytes. This area was termed the gate of immunocytes. Since monocytes are approximately 15 to 25 μm in diameter the SVF population within this gate are most probably of the same size range.

As can be seen in Table 5 similar quantities of nucleated cells were isolated from fat using enzymatic and mechanical cell isolation methods. In spite of vigorous washing, cell isolation without enzymatic or mechanical disruption of fat resulted in significantly lower quantities of cells.

Additionally, seeding of identical quantities of SVF cells at day 0 resulted in significantly higher numbers of adipose derived stromal cells after 7 days of culture when enzymatic and mechanical isolated cells were used compared to cells that were isolated by washing only (Table 5).

TABLE 5

| Isolation method | Nucleated cells per 1 ml fat (lipoaspirate) | Dead cells (percent) | Cells/well of a 6 well plate (after 7 days in culture) | Cultured cells per 1 ml fat (after 7 days in culture) |
|---|---|---|---|---|
| Enzymatic | $2.3 \times 10^5$ | 10% | $1.33 \times 10^5$ | $4.07 \times 10^5$ |
| Mechanical disruption | $1.33 \times 10^5$ | 15% | $1.56 \times 10^5$ | $2.76 \times 10^5$ |
| Wash | $0.19 \times 10^5$ | 0.1% | $0.36 \times 10^5$ | $0.09 \times 10^5$ |

Importantly, cell yield per 1 ml of fat following culture was 45 and 30 fold higher in enzymatically and in mechanically isolated cells compared to cells that were isolated by washing only (Table 5).

Seeding of identical quantities of SVF cells resulted in significantly higher yield of stromal cells following 7 days culturing when enzymatic and mechanical isolated SVF cells were used compared to cells that were isolated by washing only. This indicates that a different composition of cell populations was isolated by the different cell isolation techniques.

TABLE 6

| Surface Marker expression | Enzymatic isolation | Mechanical isolation | Wash |
|---|---|---|---|
| CD31− CD34− | 11 | 24.4 | 34.3 |
| CD31− CD34+ | 60 | 74 | 64 |
| CD31+ CD34+ | 28 | 0.4 | 0.7 |
| CD31+ CD34− | 0.5 | 0.5 | 0.5 |
| CD73+ CD29+ | 55 | 64.3 | 42 |
| CD73− CD29+ | 25.5 | 1.3 | 0 |
| CD73− CD29− | 10 | 25 | 37 |

To better define the cell composition of SVF cells isolated by the different techniques their surface marker expression was determined by an 8 color flow cytometry panel. Examination of the percent of CD45 (+) cells within SVF cells isolated by the different techniques revealed a lower (77%) percent in enzymatically isolated cells compared to cells that were isolated mechanically or by wash yielding 91% and 90% respectively of CD45(+) cells. Since mesenchymal stem cells arise solely from the CD45(−) population, representing none-hematopoietic cells, the expression of additional surface marker was examined in this population. As can be seen in Table 6 a significant percent (28%) of CD31(+) CD34(+) double positive cells was observed in enzymatically isolated cells while in both mechanically isolated cells and cells isolated by a wash this population practically did not exist.

An additional population that was hardly apparent in both mechanically and wash isolated cells was CD73(−) CD29 (+) cells. Again a significant percent (25%) of enzymatically isolated cells expressed CD73(−) CD29 (+). Thus, a significant difference in the composition of cells was demonstrated between enzymatically isolated SVF cells and mechanically isolated cells or cells isolated by a washing.

Table 6 demonstrates the differences in the percent of surface marker expression amongst CD45 (−) cells between SVF cells isolated from fat by enzymatic digestion (collagenase), mechanical disruption of fat or by washing the fat. Despite the apparent similarity in the surface marker expression between mechanically isolated and wash isolated cells a substantial difference exists between these cells as was evident in the increased culture expansion of mechanically isolated cells. Therefore, the surface marker expression between the cells isolated by these two techniques was further examined.

Table 7 shows differences in the percent of surface marker expression amongst CD45 (−) between SVF cells isolated from fat either by a mechanical disruption of fat or by fat washing. As can be seen in Table 7 a substantial increase in both CD31(−) CD34 (+) (10% increase) and in CD73 (+) CD29 (+) (20% increase) populations was evident in mechanically isolated cells compared to cells isolated by washing).

TABLE 7

| Surface Marker expression | Mechanical isolation | Wash |
|---|---|---|
| CD31− CD34− | 24.4 | 34.3 |
| CD31− CD34+ | 74 | 64 |
| CD31+ CD34+ | 0.4 | 0.7 |
| CD31+ CD34− | 0.5 | 0.5 |
| CD73+ CD29+ | 64.3 | 42 |
| CD73− CD29+ | 1.3 | 0 |
| CD73− CD29− | 25 | 37 |

The CD45(−) CD31(−) CD34(+) population is the population that harbors most adipose derived stem cell progenitor cells. As can be seen in Table 7, the mechanically isolated cell fraction has a higher percent of CD45(−) CD31(−) CD34(+) compared to cell isolated by washing, pointing to their increased ability to form Adipose-Derived Stem Cells (ASCs). Additional surface markers suggested representing ASC progenitor cells within the SVF population are CD73 and CD29. As can be seen in Table 7, mechanically isolated cells have a 20% increase in CD45(−) CD31(−) CD73(+) CD29(+) cells compared to cells isolated by washing.

Figure 5A:
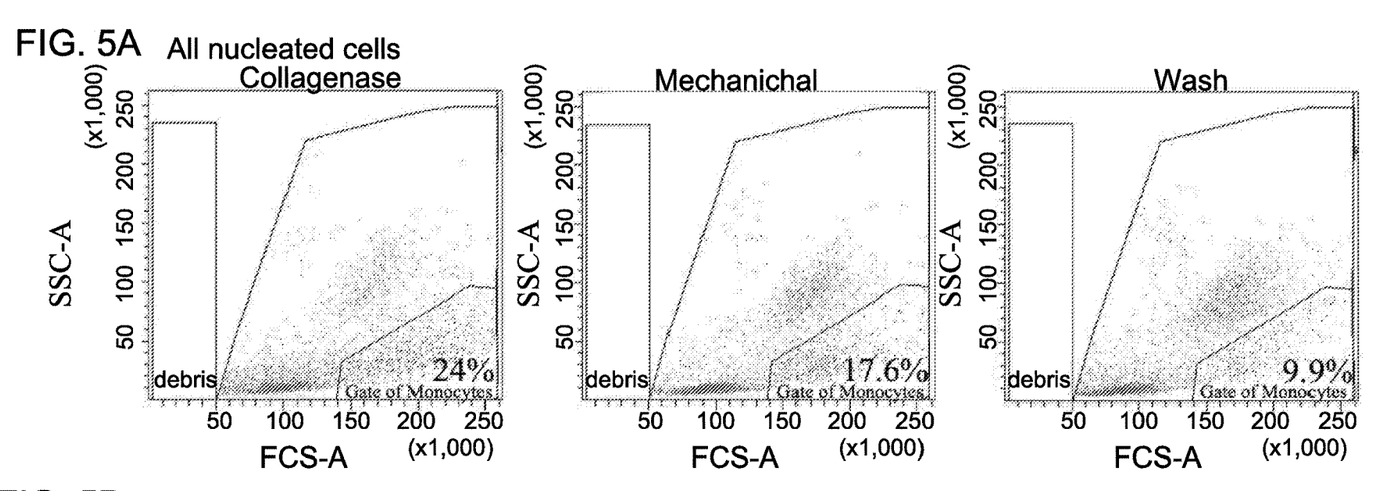
FIGS. 5A-B depict SVF isolated by enzymatic digestion or mechanical disruption of fat displaying an enriched population of CD45 (−) cells in the "gate of monocyte".
Figure 5B:
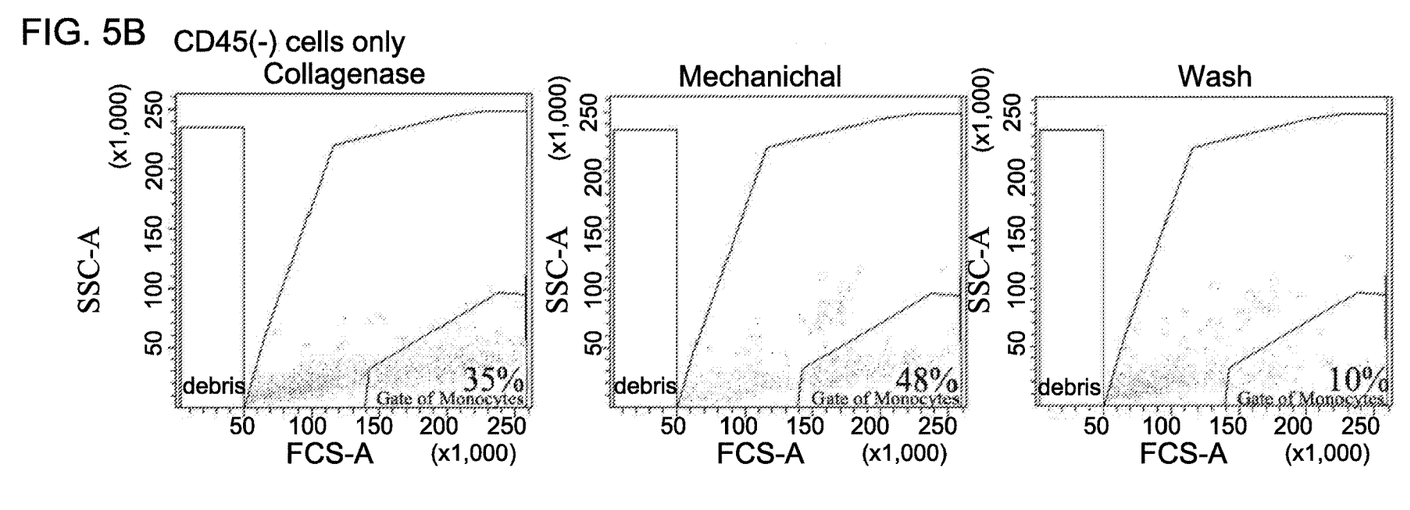

Examination of the cell distribution of the entire SVF using the forward light scatter area (FSC-A) and the side scatter area (SSC-A) parameters revealed an increased proportion of cells in a gate termed "gate of monocytes" in enzymatic and mechanical isolation compared to washing (FIG. 5A). The superior proportion of cells in the "gate of monocytes" in enzymatically and mechanically isolated cells was even more pronounced in the more relevant CD45(−) population reaching a 5 fold increase in mechanically isolated cells compared to cells isolated by washing (FIG. 5B).

The SSC-A on FCS-A distribution of all nucleated live cells (FIG. 5A) or CD45 (−) cells (FIG. 5B) of enzymatic, mechanical and wash isolated cells is displayed in a dot plot Importantly, as can be seen in Table 8, most of the CD45(−) cells within the "gate of monocytes" were CD31 (−) CD34(+), which harbor adipose stem cell progenitor cells.

Therefore, the present invention provide a new cell population within SVF termed "CD45(−) CD31(−) gate of monocytes (+) CD34 (+)". This novel population, which takes into account both the physical properties of the cells and their surface marker expression, comprise 6.6%, 4.3% and 0.88% of the total nucleated cells in enzymatically, mechanically and wash isolated cells respectively. This population comprises the majority of adipose stem cell progenitor cells as it predicts well the ratio of ASCs yields, produced from an equal number of SVF cells, after 7 days in culture (Table 8). Thus, the most profound difference between mechanically and wash isolated cells is in their CD45(−) CD31(−) gate of monocytes (+) CD34 (+) population as is summarized in Table 9. It is generally accepted that the therapeutically relevant cell population is the one that is able to produce cultured adipose derived stem cells, namely the stem cell progenitor cells. The present invention defines a subclass of stem cell progenitor cells within SVF defined using the physical properties of the cells (gate of monocyte). Thus, the CD45(−) CD31(−) gate of monocytes (+) CD34 (+) population define the most therapeutically relevant population stem cell progenitor cells within SVF. The large increase in the CD45(−) CD31(−) gate of monocytes (+) CD34 (+) cell population in mechanically isolated SVF cells compared to wash isolated cells (Table 9) suggest the increased therapeutic efficacy of mechanically isolated cells.

TABLE 8

| Surface Marker expression | Enzymatic isolation | Mechanical isolation | Wash |
|---|---|---|---|
| CD31− CD34− | 3 | 2.7 | 12 |
| CD31− CD34+ | 82 | 94 | 88 |
| CD31+ CD34+ | 13 | 0.4 | 0 |
| CD31+ CD34− | 0.5 | 0.5 | 0.5 |

TABLE 9

| Population | Mechanical isolation | Wash | Ratio Mecha/Wash |
|---|---|---|---|
| CD45 (−), CD31(−), Gate of monocytes (+), CD34+ | 4 | 0.88 | 4.54 |

Conclusions

In contrast to SVF cells that are isolated by washing, mechanically isolated cells demonstrate improved properties being similar to enzymatically isolated cells which are considered to date to be the gold standard. This is demonstrated in the following properties:

1. The Numbers of nucleated cells that are isolated from fat: Mechanical disruption of fat results in SVF cell quantities similar to quantities obtained using collagenase isolation. This was in contrast to SVF cells that were isolated by washing (without Mechanical disruption) that demonstrate significantly lower quantities.
2. Expansion ability: culture expansion of mechanically isolated SVF yielded cell quantities similar to the quantities obtained using collagenase isolated cells after both 7 and 14 days. This was in contrast to SVF cells that were isolated by washing which demonstrated significantly lower expansion in culture.
3. Differentiation potential: mechanically isolated cells demonstrated differentiation capabilities to both bone and fat. The fat differentiation ability of mechanically isolated cells was far superior to that of cells isolated by washing.
4. Surface markers expression of cultured SVF cells: At passage 0, mechanically isolated cells demonstrated the expected mesenchymal stem cells surface marker expression pattern.
5. The proportion of CD45(−) CD31(−) gate of monocytes (+) CD34 (+) cells in SVF: the data demonstrate a large increase in the proportion of cells within this population in mechanically isolated cells compared to wash isolated cells that correlates with their increased ability to produce adipose stem cells.

Example 5

Figure 6:
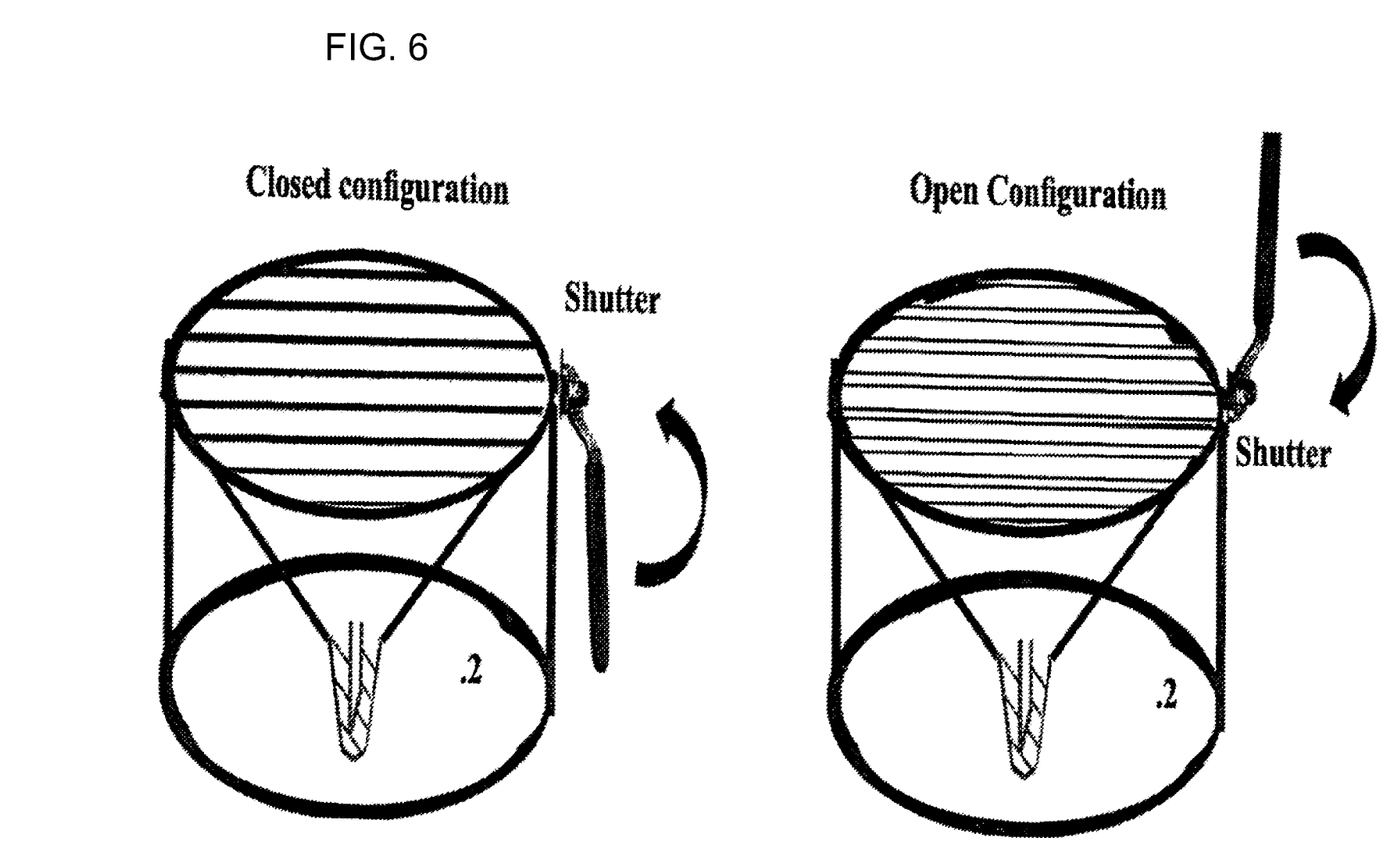
FIG. 6 depicts a device for the mechanical isolation of stromal vascular fraction (SVF) cells by pressure filtration. The device is constructed of two spreadable containers designated 1 and 2.
Figure 7:
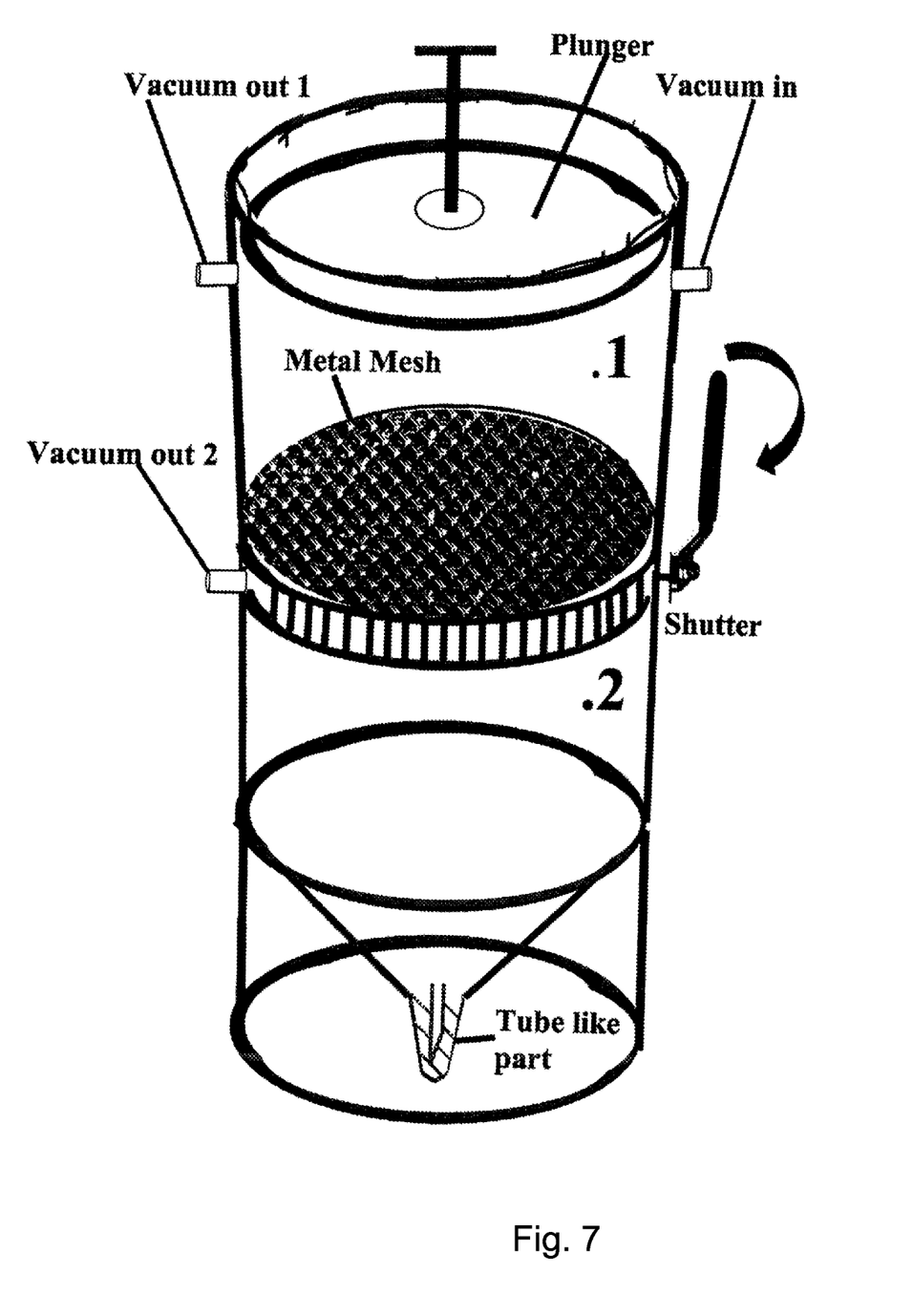
FIG. 7 depicts a device for the mechanical isolation of stromal vascular fraction (SVF) cells by pressure filtration in which the two containers are separated by a shutter that has a closed and an open position.

Turning to a further device of the invention depicted in FIGS. 6 and 7. A device is depicted for the mechanical isolation of stromal vascular fraction (SVF) cells by pressure filtration. The device in FIG. 6 is constructed of two spreadable containers designated 1 and 2. The two containers are separated by a shutter that has a closed and an open position (FIG. 7).

According to an exemplary embodiment, the process for SVF cells isolation comprises one or more of the following steps:
1. The shutter is in a closed position and the two containers are connected.
2. A liposuction device is connected to vacuum in. Suction pump is connected to Vacuum 1 and liposuction is performed into container 1.
3. At the end of the liposuction procedure the lipoaspirate is left to settle for 5 minutes.
4. The vacuum pump is then connected to vacuum out 2 and the liposuction fluid is vacuumed out.

5. Sterile fluid is then added to the fat from the vacuum in spot, the container is turned upside down a couple of times and the lipoaspirate is left to settle 5 minutes again.
6. The liquid is again vacuumed from vacuum out 2.
7. Sterile fluid is added to the fat from the vacuum in spot and the fat is mixed with fluid.
8. Container is turned upside down a couple of time to mix the fat with fluid.
9. Shutter is changed immediately to open position and fat is passed through the metal mesh by pressuring down the plunger.
10. Once all the fat and fluid were passed through the filter into container 2 the shutter is put to a closed position.
11. Access fluid from above the closed shutter is vacuumed out.
12. Container 2 is detached from container 1 and the fat remains sterile because the top end is closed by the closed shutter.
13. Container is centrifuged and SVF cells are concentrated at the tube like part at the bottom of the container.
14. SVF cells are sterilely isolated by a needle and syringe.

The invention claimed is:

1. A method for enriching a cell population from a mammalian adipose tissue, the method comprising:
aspirating adipose tissue into a container assembly using an aspiration tube having a proximal end detachably connected to the container assembly and a distal end inserted into at least one cavity of a mammalian body;
electrically actuating a mechanical tissue disruption device, while the mechanical tissue disruption device is positioned within the container assembly, with an electrical actuator that is detachably connected to the mechanical tissue disruption device for said electrically actuating, wherein the mechanical tissue disruption device comprises at least one rotatable blade that rotates, when the mechanical tissue disruption device is electrically actuated, to disrupt/rupture the adipose tissue in the container assembly to obtain a cell suspension, wherein the disruption does not utilize an enzyme;
optionally washing the suspension of cells within the container assembly; and
transferring the container assembly, with the suspension of cells being within the container assembly, into a centrifuge and centrifuging the container assembly to thereby obtain a cell pellet from the suspension of cells within the container assembly, and extracting the cell pellet from within the container assembly, and removing the container assembly from the centrifuge;
to thereby obtain an enriched cell population.

2. The method of claim 1, wherein the adipose tissue aspirated into the container is washed prior to mechanical disruption/rupturing.

3. The method of claim 1, wherein following mechanical disruption/rupturing the cell pellet is extracted following phase separation.

4. The method of claim 1, wherein the mechanical disruption/rupturing is carried out in lipoaspirate solution without the addition of a washing solution.

5. The method of claim 4, wherein the suspension of cells is washed following mechanical disruption/rupturing.

6. The method of claim 4, wherein the suspension of cells are not washed following mechanical disruption/rupturing and wherein the cell pellet is extracted following phase separation.

7. The method of claim 5, wherein the suspension of cells is washed with a washing solution, the washing solution containing at least one additional reagent selected from a cell specific antibody, a buffering agent, a sugar based density gradient, a non-sugar density gradient, an antibody mediated magnetic cell sorting solution and a non-magnetic antibody mediated cell sorting solution.

8. The method of claim 1, wherein the enriched cell population is further processed to enrich for a specific cell population.

9. The method of claim 1, wherein the enriched cell population is a stromal cell fraction (SVF).

10. The method of claim 9, wherein the SVF is characterized by at least one of the following:
having a percentage of between about 7 and about 40 of CD45(−) CD31(−) CD34(+) and between about 6 and about 30 of CD45(−) CD73(+) CD29(+) cells; and/or
having a percentage of between about 4 and about 10 of CD45(−) CD31(−) gate of monocytes(+) CD34(+) cells.

11. The method of claim 9, wherein the SVF is characterized by:
having a percentage of between about 7 and about 40 of CD45(−) CD31(−) CD34(+) and between about 6 and about 30 of CD45(−) CD73(+) CD29(+) cells; and
having a percentage of between about 4 and about 10 of CD45(−) CD31(−) gate of monocytes(+) CD34(+) cells.

12. The method of claim 9, wherein the SVF is characterized by having a percentage of between about 7 and about 40 of CD45(−) CD31(−) CD34(+) and between about 6 and about 30 of CD45(−) CD73(+) CD29(+) cells.

13. The method of claim 9, wherein the SVF is characterized by having a percentage of between about 4 and about 10 of CD45(−) CD31(−) gate of monocytes(+) CD34(+) cells.

14. The method of claim 9, further comprising a step of isolating fat from which the SVF was obtained.

15. The method of claim 1, wherein the adipose tissue is not a liquid.

16. The method of claim 1, wherein the container assembly is provided with the mechanical disruption device.

17. The method of claim 1, wherein the blades are in contact with the tissues.

18. The method for enriching a cell population from a mammalian adipose tissue as recited in claim 1, further comprising washing the suspension of cells within the container assembly.

19. The method for enriching a cell population from a mammalian adipose tissue as recited in claim 1, wherein the suspension of cells is not washed within the container assembly.

20. The method of claim 1, wherein the mechanical tissue disruption device comprising the at least one rotatable blade disrupts/ruptures the adipose tissue that has been directly aspirated into the container assembly via the aspiration tube, thereby obtaining a cell suspension from the aspirated adipose tissue that has a maintained cell viability.

21. The method of claim 1, wherein, prior to placing the container assembly in the centrifuge, processing of the adipose tissue in the container assembly consist of said mechanical disruption and optionally said washing.

22. The method of claim 1, wherein, prior to disrupting/rupturing the adipose tissue and optional washing in the container assembly, adipocytes collected into the container assembly are at most partially disrupted due to shear forces affected during suction and passage through the aspiration tube.

23. The method of claim 1, wherein once adipocytes of the adipose tissue are collected in the container assembly, the mechanical disruption of the harvested adipocytes of the adipose tissue is directly carried out using the mechanical tissue disruption device controlled by the electrical actuator that is external and detachably connected to the closing cap of the container assembly, wherein the mechanical disruption of the harvested adipocytes of the adipose tissue is carried out in either fluid aspirated during liposuction, the washing solution resulting from washing the harvested adipocytes within the container assembly, or in an isolated lipoaspirate that was separated from any added solutions.

* * * * *